United States Patent
Lemons et al.

[11] 4,028,933
[45] June 14, 1977

[54] ACOUSTIC MICROSCOPE

[75] Inventors: Ross A. Lemons, Mountain View; Calvin F. Quate, Los Altos Hills, both of Calif.

[73] Assignee: The Board of Trustees of Leland Stanford Junior University, Stanford, Calif.

[22] Filed: June 18, 1975

[21] Appl. No.: 587,817

Related U.S. Application Data

[63] Continuation of Ser. No. 442,782, Feb. 15, 1974, abandoned.

[52] U.S. Cl. .................................. 73/67.6; 73/67.7
[51] Int. Cl.$^2$ ........................................ G01N 29/04
[58] Field of Search .......... 73/67.5 R, 67.5 H, 67.6, 73/67.7, 67.8 R, 67.8 S, 67.9, 71.5 US; 340/1 R, 5 MP, 5 H, 8 L

[56] References Cited

UNITED STATES PATENTS

| | | | |
|---|---|---|---|
| 2,525,873 | 10/1950 | De Lano, Jr. | 73/67.6 |
| 2,848,890 | 8/1958 | Sheldon | 73/67.5 R |
| 2,912,853 | 11/1959 | Hanysz | 73/67.6 |
| 3,024,644 | 3/1962 | Fry et al. | 73/67.5 R |
| 3,239,801 | 3/1966 | McGaughey | 340/8 L X |
| 3,687,219 | 8/1972 | Langlois | 340/8 L X |
| 3,699,805 | 10/1972 | Bayre | 73/67.6 |
| 3,756,071 | 9/1973 | Dory | 73/67.8 R |
| 3,774,717 | 11/1973 | Chodorow | 73/67.7 X |

FOREIGN PATENTS OR APPLICATIONS

| | | | |
|---|---|---|---|
| 1,131,075 | 10/1968 | United Kingdom | 73/67.5 R |

Primary Examiner—Richard C. Queisser
Assistant Examiner—John P. Beauchamp
Attorney, Agent, or Firm—Flehr, Hohbach, Test, Albritton & Herbert

[57] ABSTRACT

A scanning acoustic microscope wherein a high frequency acoustic plane wave is focused by an acoustic lens to scan an object at the focal plane and is then recollimated by a second acoustic lens, detected with a piezoelectric detector, and the detected acoustic signal applied to an oscilloscope to provide a visual display.

34 Claims, 6 Drawing Figures

ACOUSTIC MICROSCOPE

This is a continuation, of application Ser. No. 442,782 filed Feb. 15, 1974, abandoned.

FIELD OF THE INVENTION

The present invention relates generally to the field of microscopes and, more particularly, to microscopes utilizing high frequency acoustic wave energy.

BACKGROUND OF THE INVENTION

Conventional microscopes are based on two forms of radiation, electromagnetic waves as in the optical instruments and the electron waves as in electron microscopes.

Optical instruments have been refined over a period of many years to provide accurate images of even objects as small as biological cells. Regardless of such refinements, inherent limitations exist since the optical systems basically sense the dielectric properties of the specimen or object being imaged. Because of this, certain objects are optically transparent so that no image may be developed while others are optically opaque so that interior details are unrevealed. Furthermore, there are limitations in contrast sensitivity since, for example, there is little intrinsic optical contrast in certain biological specimens such as tissue sections and cell suspensions. Such contrast limitations have been but partially overcome by the very tedious technique of staining biological specimens.

The electron microscope of course is technically much more difficult to construct and use. Additionally, certain objects such as living cells can not be examined because of the requirements for support in a vacuum and the electron bombardment which damage the cells.

The relatively recent development of acoustic wave generation at frequencies approximating 1,000 MHz provides an acoustic wavelength in water in the neighborhood of one micron and accordingly has suggested itself as a potentially excellent mechanism for the generation of high resolution images. Furthermore, it is the variation in the elastic rather than the dielectric properties of the specimen that determines the scattering, reflection, and absorption of the acoustic energy. This enables the study of details lying beneath the surface of certain specimens which would otherwise be unrevealed due to optical or electron opacity. Furthermore, and of the greatest importance, variations in the elastic properties also show different details and, in particular, provide for intrinsic acoustic contrast.

SUMMARY OF THE PRESENT INVENTION

Accordingly, it is the general objective of the present invention to provide an acoustic microscope which has high resolution, sensitivity and contrast, yet is simple both structurally and in its utilization.

To achieve this objective, radio frequency energy in the microwave region is applied to a piezoelectric transducer to generate a bulk acoustic wave in the form of a collimated beam in an acoustic propagating medium which beam is then delivered to an acoustic lens which can take the simple but effective form of a concavity in the propagating medium and which effects focusing of the acoustic energy to a focal point in an adjacent fluid medium enabling acoustic contact with a specimen or object supported in the focal plane. The acoustic lens is designed so as to have minimal spherical aberration so that the system resolution is limited only by diffraction this being a very significant feature of the invention. Scanning of the object is achieved by relative motion between the focused acoustic beam and the object which may, for example, take the simple form of a mechanical translation of the object itself in the focal plane.

Depending upon the properties of the object and, more particularly, the elastic properties thereof, the acoustic energy will be absorbed, reflected and/or scattered so as to effect pertubations in the form of intensity or phase variations in the emerging acoustic energy which thereafter is detected by the same or another piezoelectric transducer. Since perturbations in both transmitted and reflected acoustic energy exist, the detection can be of either the transmitted or reflected energy dependent upon the particular specimen being viewed.

The detected acoustic signal can be applied to an oscilloscope for visual display and the motion of the object through the mechanical scanning thereof in the focal plane of the acoustic energy can be synchronized with the scanning of the electron beam in the display oscilloscope. Furthermore, the intensity of this beam can be made proportionate to the acoustic energy transmitted by the object such that when the electon beam strikes the phosphorescent screen, the visible image is excellent.

Dependent upon the precise frequency chosen, very high resolution can be obtained. For example, if a frequency of 400 MHz is utilized, resolution will be approximately three microns and if 1.5 GHz, an ultimate resolution of less than one micron is attainable. Because of the acoustic lens design (mentioned hereinabove), spherical aberration does not provide any limit on such resolution.

Since the entire acoustic beam is utilized, a minimal amount of acoustic power is required to produce an image with excellent contrast. Furthermore, excellent signal to noise characteristics can be readily obtained at average power levels of $10^{-7}$ watts/square centimeter. Accordingly, the power required is well below the damage level for biological specimens.

Various specific arrangements for detection can be utilized. The transmitted acoustic energy can be recollimated by a similar acoustic lens and then detected by a piezoelectric transducer which provides great sensitivity. The lenses themselves can be simply provided by appropriate concavities in the medium, or a more complex lens such as the "aplanatic" can be utilized to further reduce spherical aberration, particularly in the region off the beam axis. It is contemplated that the transmission of acoustic energy over the cross-section of the lens can be controlled in such a fashion as to optimize the beam contour in the region of the waist. We have in mind a beam contour, or cross-section, that would give us the maximum phase resolution.

Reflected rather than transmitted acoustic energy can be detected either by the transmitting transducer or by a separate and appropriately positioned second lens and transducer.

Furthermore, a multiplicity of laterally-spaced transducers and lenses can be utilized with the object being moved sequentially through the units and the detected outputs, after appropriate external time delay, combined to produce ultimately a much higher signal-to-noise ratio. Various signal processing techniques can be incorporated in the process.

Additionally, since the object or specimen subjected to the acoustic wave energy effects phase variations, the phase-pertubed wave can also be compared with a phase reference signal for subsequent display.

The input energy can also be varied much in the fashion of existent radar systems to provide additional details of the object. For example, the input signal can be in the form of a "chirp" (linear swept frequency) or several input signals at different frequencies can be sequentially applied to the object and subsequently recombined. A color display oscilloscope with different color representations to provide additional contrast in the ultimate visual image is one example.

Furthermore, the object can also be supported for motion along the direction of the acoustic energy thus to bring various sections of the object into the focal plane, enabling, for example, detection of internal variations in the object.

Additionally, a reference wave may be provided in the manner of acoustic holography so as to provide a three-dimensional picture.

BRIEF DESCRIPTION OF THE DRAWING

The stated objective of the invention and the manner in which it is achieved, as summarized hereinabove will be more readily understood by reference to the following detailed description of several specific embodiments of the invention shown in the accompanying drawings wherein.

DETAILED DESCRIPTION OF THE EXEMPLARY EMBODIMENTS OF THE INVENTION

Figure 1:
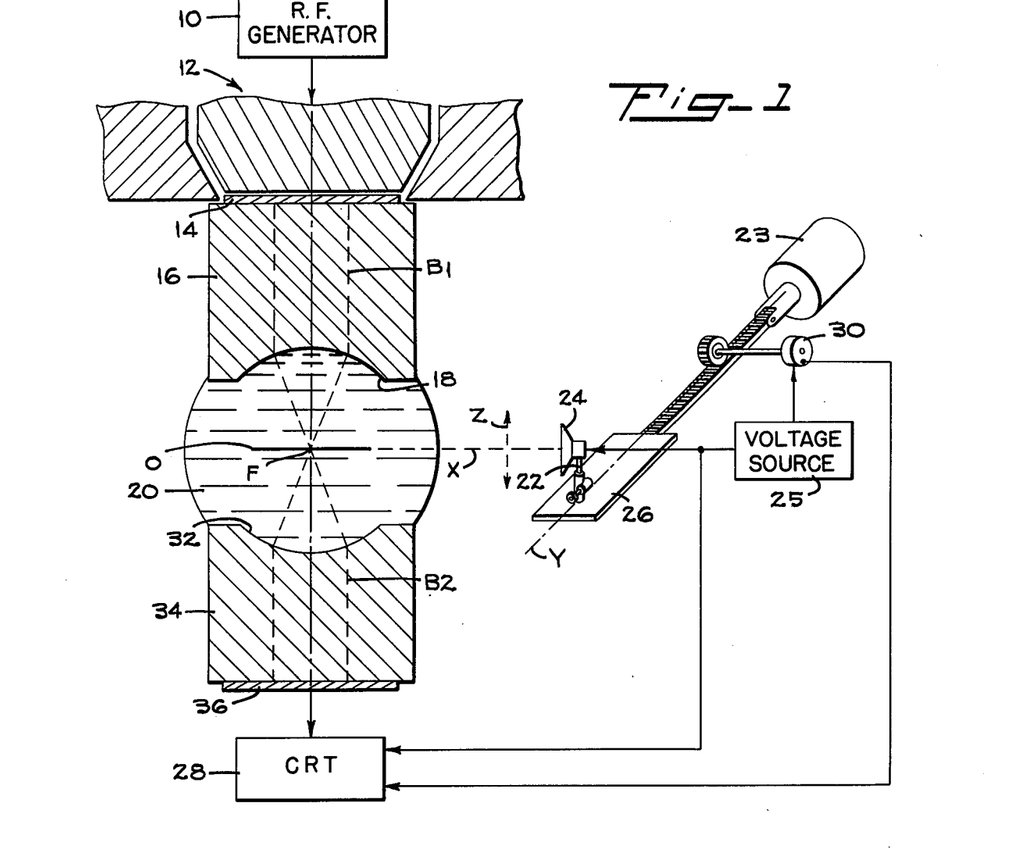
FIG. 1 is a diagrammatic central sectional view of an acoustic microscope constituting one embodiment of the present invention with the associated electronic input and output components illustrated in block diagram form, FIG. 2 constitutes a diagram explanatory of the operation of an acoustic lens as utilized in the FIG. 1 arrangement.

With initial reference to FIG. 1, a radio frequency generator 10 is arranged to deliver electromagnetic energy at a frequency of, for example, 400 MHz through a coaxial line 12 whose terminal end delivers energy to a thin film or plate piezoelectric transducer 14 at the end of an acoustic propagating medium 16 so as to generate a bulk acoustic wave in the form of a collimated beam indicated at $B_1$.

The transducer 14, in the present instance, can be formed of a thin film of zinc oxide, but other piezoelectric materials such as lithium niobate, Cadmium sulphide, zinc sulphide or many other piezoelectric materials can be utilized as is well known to those skilled in the art. In turn, the acoustic propagating medium 16, in the present instance, constitutes sapphire but other acoustic propagating mediums such as fused quartz, yttrium aluminum garnet, a piezoelectric semiconductor such as Cadmium sulphide, or other known propagating mediums can be substituted therefor. However, for purposes of the present invention, it is preferred to utilize a propagating medium that has a rather high acoustic propagation velocity as will be explained in more detail hereinafter.

An acoustic lens 18 is formed at the extremity of the propagating medium 16 remote from the input transducer 14 and, as specifically illustrated, takes the simple form of a polished concave spherical surface ground into the end of the sapphire material. More particularly, the illustrated lens was ground with a 0.4 millimeter radius of curvature with an $f$ number of 0.65. Accordingly, the collimated acoustic beam $B_1$ is arranged to converge into an adjacent fluid medium 20 which in the present instance constitutes water. Since the water is a slower velocity acoustic medium than the sapphire, the acoustic lens constitutes a positive lens which focuses the beam to a focal point indicated at F.

Figure 2:
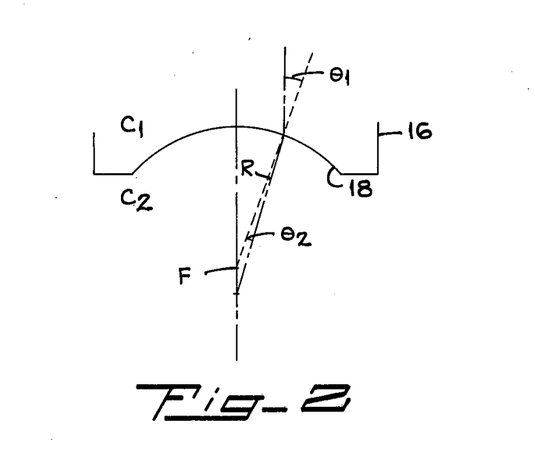

Since the sapphire has a much higher acoustic velocity than does water, the velocity ratio $C_1/C_2$ of these materials is approximately 7.45, so that the angle, $\theta_2$ between the refracted ray of acoustic energy and the intersecting radius R of the lens 18 as indicated in FIG. 2 is reduced to a small value which, of course, is determined by Snell's Law which states that $\sin \theta_2 = C_2/C_1 \sin \theta_1$ where $\theta_1$ is the angle between the impinging ray and the extension of the radius of curvature as indicated in FIG. 2. Accordingly, with the sapphire and water media, the diameter of the circle of least confusion is reduced to less than one micron so that the spherical aberration of the lens 18 limits the resolution capabilities of the described acoustic microscope to the value of one micron or less. In the present instance, where the frequency of operation is 400 MHz the acoustic wavelength in water is approximately 3.75 microns so that no practical limitation on the resolution results from the minimized spherical aberration of the lens. Special coatings on the lens can be used to further reduce the circle of least confusion.

As previously mentioned, the object or specimen O to be viewed is supported in the fluid medium 20 at the focal point F and means are provided to provide for scanning, in the present instance by the simple mechanical motion of the specimen. As diagrammatically indicated in FIG. 1, an adjustable support 22 using a micrometer allows adjustment of the specimen or object O into or out of the focal plane which shall be termed the Z direction. In turn, in the focal plane, a fast scan in what is indicated as the X direction in FIG. 1 is provided by mounting on the support 22 a speaker indicated at 24 to whose cone the specimen or object is connected. The support 22, in turn, is mounted on a stage 26 which can be hydraulically reciprocated in the indicated Y directions. The same voltage that drives the speaker 24 is also delivered to the horizontal deflection control of a conventional oscilloscope 28 and the reciprocal stage is connected to a potentiometer 30 whose output voltage is delivered to the vertical deflection electrode of the oscilloscope 28 thus providing a one-to-one correspondence between the position of the object and the oscillocope beam position. As a practical matter, up to a three millimeter field of view with scan rates of 300 lines/second can be achieved so that a complete image can be formed on the oscilloscope in less than one second.

In a known fashion, the acoustic energy impinging upon the object O at any time will be perturbed so that acoustic variations in intensity and/or phase will result depending upon particular elastic properties of the specimen being viewed and the perturbed acoustic energy is then transmitted through the water to another acoustic lens 32 which preferably is identical to the first acoustic lens and positioned so that the foci of the two lenses 18, 32 are coincident. The propagating medium 34 upon whose extremity the acoustic lens 32 is formed recollimates the acoustic energy which is transmitted through such medium as indicated at $B_2$ and is delivered to a thin film piezoelectric transducer 36 of zinc oxide or any other suitable piezoelectric material which accordingly functions as detector of the perturbed acoustic energy. The energy is converted by the transducer to electromagnetic energy which in turn is delivered to the cathode ray tube to modify the intensity of its display beam thus to provide the ultimate visible display of the object image.

Since all of the power diverging from the object point is utilized, very low acoustic power densities can be utilized in the described microscope. As a practical matter, average sound intensity levels of less than $10^{-7}$ watts per square centimeter have provided images of biological specimens with excellent contrast. Such power levels are below the damage threshold of such specimens. Furthermore, experimental results have indicated excellent contrast resultant from the elastic properties of the specimens or objects being viewed and, as previously indicated, with the operating frequency of 400 MHz, a resolution of approximately three microns has been attained. It will be apparent that if the frequency is increased above 1,000 MHz, a resolution approaching one micron will be attainable and it should be re-emphasized that the spherical aberration of the acoustic lenses is such that no limitation on this potential resolution exists.

Figure 3:
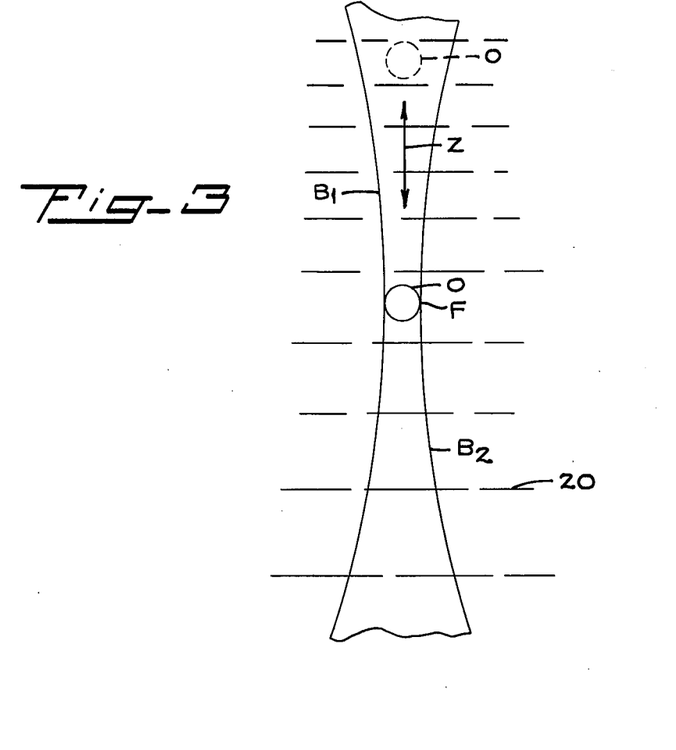
FIG. 3 is a diagrammatic showing explanatory of the acoustic detection of interior object details as attained by the FIG. 1 apparatus.

If the object position is shifted in the Z direction by the micrometer-controlled adjustable support 22, it will be apparent that the object position relative to the focal plane will be changed and a different portion of the object will lie at the focal plane, or at the narrow "waist" (e.g. one micron) of the acoustic beam. As shown in FIG. 3, if a one micron object O is disposed at the focal point F, substantially the entire beam will be intercepted and maximal perturbation will exist. However, even a slight Z direction adjustment of the object O to the dotted line position will reduce the beam interception and resultant perturbation greatly, and if displaced sufficiently it will no longer be observed. However, if the object has a considerable dimension in the Z direction, the shifting will bring a portion of the object at a different depth into the focal plane so that it will be specifically detected. Thus, interior details of an object can be readily examined.

As has been mentioned, interception of an acoustic beam by an object or specimen produces reflections as well as perturbations in both intensity and phase of the transmitted energy, and such reflected energy can, in accordance with the general principle of the present invention, be utilized to produce a visible image. Some such reflected energy will, of course, be returned to the input transducer of FIG. 1 and can thereafter be delivered to an oscilloscope for display.

Figure 4:
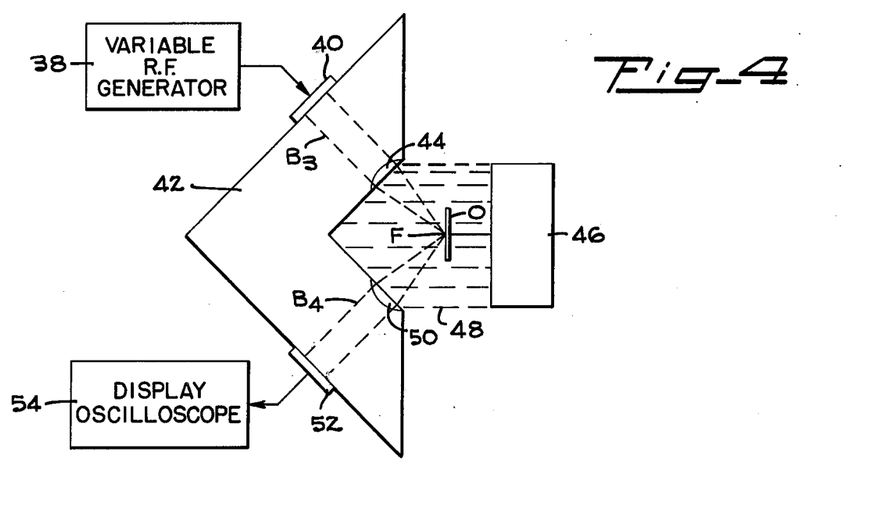
FIG. 4 is a diagrammatic cross-sectional view of a modified embodiment wherein reflected acoustic energy is detected.

The alternative apparatus diagrammatically shown in FIG. 4 has the advantage of isolating the incident and reflected power. More particularly, a variable radio frequency generator 38 delivers acoustic input energy to a first transducer 40 on one face of a prism-like propagating medium 42 to generate a collimated beam $B_3$ which is subsequently focused by an acoustic lens 44 to a focal point F whereat the specimen or object O can be supported by a suitable support 46 in a fluid medium 48 which can be water as in the first embodiment or other fluid such as liquid helium having yet a slower acoustic velocity, reducing both wavelength and spherical aberration. The energy reflected by the object O is recollimated in a reflected beam $B_4$ by a second acoustic lens 50 appropriately positioned in the propagating prism 42 so the energy can then be detected by a second output transducer 52 and delivered to a display oscilloscope 54 in a fashion generally analogous to the first embodiment of the invention.

However, the variable radio frequency generator 38 can be operated to generate a linear-swept input signal of the type generally referred to as a "chirp" in sophisticated radar operations and in an analogous fashion, significant details of the object can thus be imaged.

Furthermore, the generator 38 or several separate generators operating at different frequencies can have several signals delivered to the input transducer 40 and separately delivered to the oscilloscope 54 which can take the form of a multi-color unit enabling the individual color display of the different frequency signals and a display image constituting the combination thereof thus providing in certain instances more information about the object.

Figure 5:
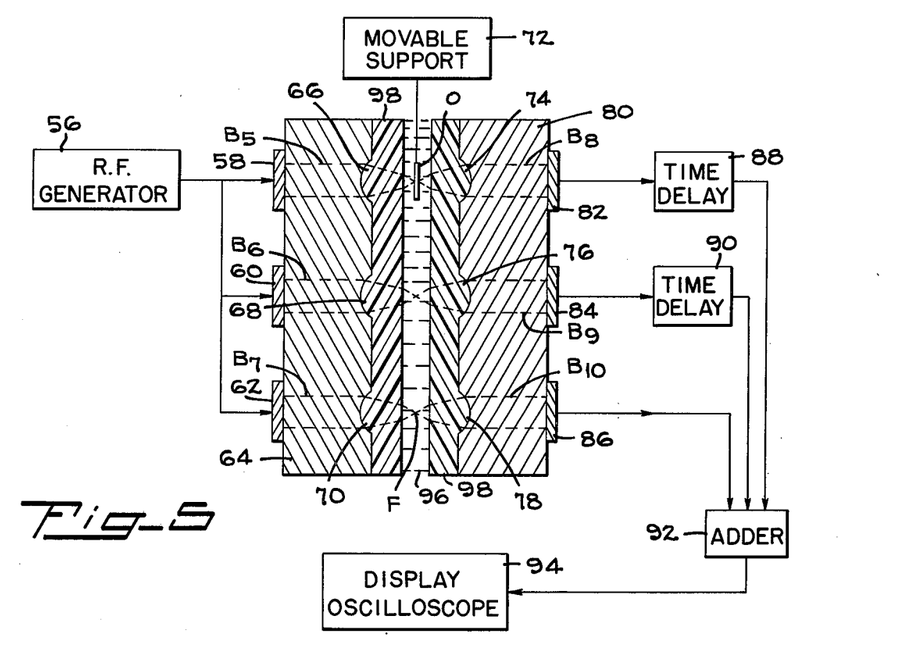
FIG. 5 is a similar view of a third embodiment wherein multiple detection is provided.

The described embodiments employ but a single input acoustic beam, but certain advantages, such as a significant improvement in signal-to-noise ratio can be obtained by exposing the object in appropriate sequence to series of beams. For example, as shown in FIG. 5, input energy from a single radio frequency generator 56 is applied to three input transducers 58, 60, 62 preferably in laterally spaced relation to a single propagating medium 64 thus to form three parallel beams, $B_5$, $B_6$, and $B_7$, which are focused by three identical lenses 66, 68, 70 into focal points located in a common focal plane F. The object O is mechanically scanned by a suitable support 72 through the three focused beams to perturb the same in a predetermined time sequence. The perturbed input signals are recollimated into three output beams $B_8$, $B_9$, and $B_{10}$ by acoustic lenses 74, 76, 78 formed in a single output propagating medium 80 which carries appropriately positioned transducers 82, 84, 86 for detection of the three separate outputs. It is assumed that the object O is mechanically moved downwardly as viewed in FIG. 5, variable time delay units 88 and 90 are set to delay delivery of the first and second output signals so that all three will be delivered to electronic adder 92 and the combined output then be delivered to a display oscilloscope 94. The "noise" generated in the three units builds up in an incoherent fashion but the object signals from the three are additive, thus improving the signal-to-noise ratio in proportion to the number of units employed.

The object O is still moved through a fluid medium 96, but to assure precision of its position in the common focal plane, guide members 98 having flat interior surfaces are mounted on the propagating structures 64 and 30. These guide members 98 should be formed of epoxy or other material having low acoustic loss characteristics and such low-loss inserts can obviously be used to advantage in any of the other embodiments of the invention.

Figure 6:
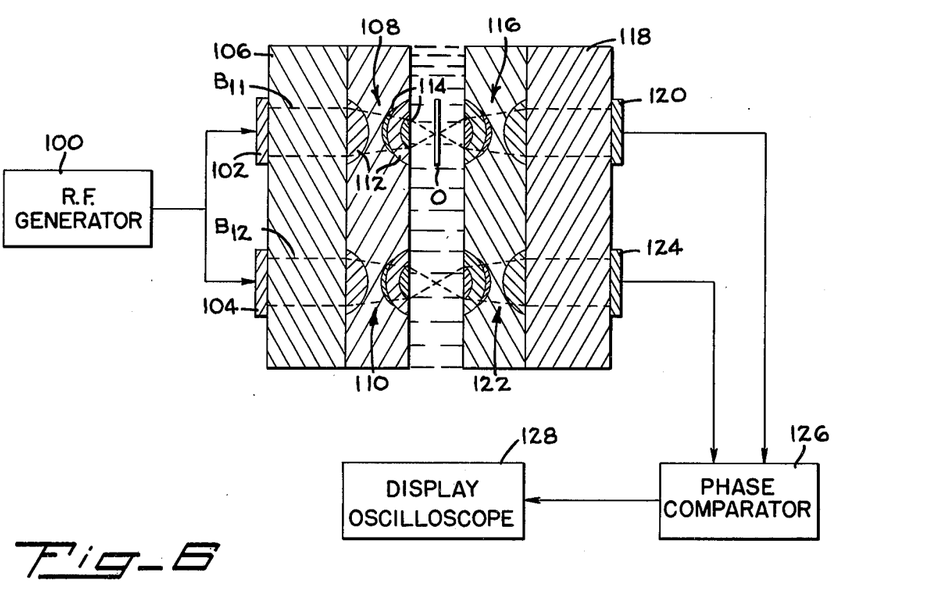
FIG. 6 is a similar view of another embodiment wherein phase perturbations of the acoustic energy are detected and displayed.

In the previously described embodiments, the detection and resultant image has been predicated primarily on the varied intensity of the transmitted or reflected acoustic energy resultant from the interposition of the specimen or object in the path of acoustic energy. As indicated, phase variations also occur, and these can be utilized to ultimately generate a visible image. For example, with specific reference to FIG. 6, radio frequency energy from a single generator 100 is simultaneously delivered to two transducers 102,104 on the same surface of a lithium niobate propagating medium 106 to generate two similar acoustic beams $B_{11}$, $B_{12}$, which are focused by like acoustic lenses 108, 110, which could each take the form of simple concavities in the lithium niobate, but each, as shown, is a compound aplanatic lens including appropriately ground fused quartz 112 with intervening layers of gallium 114 so as to reduce spherical aberration to a nullity in a fashion well known in the art. The object O is exposed at the focal point of one beam $B_{11}$ and the phase-perturbed output recollimated by another lens 116 adjacent a propagating crystal 118 for delivery to a detecting transducer 120. The other beam $B_{12}$, after focusing, is recollimated by a similar lens 122 and detected by a corresponding transducer 124, both outputs then being delivered to a standard phase comparator 126 whose output is, in turn, delivered to a display oscilloscope 128 which develops the visual image.

Obviously, many additional modifications and/or alterations on this structure as described can be made without departing from the spirit of the invention and the foregoing description of one embodiment is to be considered as purely exemplary and not in a limiting sense. The actual scope of the invention is to be indicated only by reference to the appended claims.

What is claimed is:

1. An acoustic microscope for producing an image of an object of interest utilizing high frequency acoustic wave energy, comprising:
   a. transducer means for generating acoustic energy at a frequency of at least 100MHz.
   b. means forming a first solid acoustic energy propagating medium having a predetermined acoustic velocity C1 disposed adjacent said acoustic energy generating means, said transducer means and propagating medium forming a collimated beam of acoustic energy;
   c. a first acoustic lens means disposed adjacent the other end of said acoustic energy propagating medium, said acoustic means forming a focal point outside of said acoustic energy propagating means, said lens having a predetermined $f$ number;
   d. a fluid acoustic energy propagating medium having a predetermined acoustic velocity C2, disposed adjacent said acoustic lens means and within which an object to be observed may be positioned, said fluid medium having an acoustic velocity to provide a wavelength of said acoustic energy of about 15 microns or less in said medium and substantially less than the acoustic velocity of said acoustic energy propagating medium, said velocity C1 and C2 being chosen such that their ratio produces an acoustical optical system having negligible spherical aberration;
   e. means for moving, relatively, said object to be observed with respect to the beam such that the focal point of said acoustic lens occurs on the surface or within the object to be observed;
   f. a second solid acoustic energy propagating medium in contact with the fluid medium and having a concavity therein forming a second acoustic lens whose focal point is coincident with said first acoustic lens; and
   g. a piezoelectric transducer located on the end of said second acoustic propagating medium remote from said second acoustic lens for detecting the acoustic energy perturbed by said object so that an image of the object of interest is obtainable.

2. An acoustic microscope according to claim 1 wherein said first and second acoustic propagating media each has an acoustic velocity at least double that of said fluid medium.

3. An acoustic microscope according to claim 1 wherein said first and second acoustic propagating media each constitutes a solid having a spherical concavity at one end thereof to form said acoustic lens with a radius of curvature of substantially 400 microns.

4. An acoustic microscope as in claim 1 wherein said first and second acoustic lenses are aplanatic.

5. An acoustic microscope as in claim 1 wherein said second acoustic propagating medium, said second acoustic lens and the piezoelectric transducer are disposed to detect acoustic energy transmitted beyond the object.

6. An acoustic microscope as in claim 1 wherein said second acoustic propagating medium, said second acoustic lens and the piezoelectric transducer are disposed to detect acoustic energy reflected by the object.

7. An acoustic microscope according to claim 1 further including a radio frequency generator operating in the microwave frequency region of the electromagnetic spectrum and connected to the transducer means.

8. An acoustic microscope as in claim 1 further including a radio frequency generator that generates a chirp output that drives the transducer means.

9. An acoustic microscope as in claim 1 further including means for phase comparing the output of a radio frequency generator with the detected acoustic signal perturbed by the object.

10. The apparatus of claim 1 wherein said detector means including means for obtaining a visible image of the object.

11. An acoustic microscope according to claim 10 wherein said visual-image display means includes an oscilloscope.

12. An acoustic microscope according to claim 11 wherein
    said oscilloscope is operative to provide several color displays, and which comprises
    means for generating several acoustic beams at different frequencies,
    means for detecting the different perturbed acoustic signals resultant from the several acoustic beams at different frequencies, and
    means for delivering said different acoustic signal to said oscilloscope for visual display in different colors.

13. The apparatus of claim 10 wherein said image means includes means to contrast the image corresponding to changes of electrical signals proportional to perturbed acoustical energy by the object in relation to the relative position of said object to said acoustic beam.

14. The apparatus of claim 13 wherein the moving means translates said object through the focal point of said lens in two mutually perpendicular directions.

15. The apparatus of claim 1 including means for moving said object in the direction of the propagating acoustic waves.

16. The apparatus of claim 13 wherein said moving means translates said object in a raster pattern and said detector means includes a CRT display raster synchronized to the translational movement of said object.

17. A microscope for obtaining a two dimensional, pictorial representation of an object of interest by scanning the object with ultrasonic acoustic waves, comprising:
   a. a first acoustic medium wherein ultrasonic acoustic waves are propagated;
   b. a concavity forming a first acoustic lens at the end of said first propagating medium;
   c. means for generating ultrasonic acoustic waves in the first propagating medium, said waves being directed toward the acoustic lens and focused thereby to a waist having a microscopic cross-sectional area, said waves having a frequency of at least 100 MHz;
   d. a second acoustic medium wherein ultrasonic waves are collimated;
   e. a concavity forming a second acoustic lens at the end of said second propagating medium, said first and second acoustic lenses having coincident foci;
   f. transducer means for converting the acoustic waves in the second acoustic medium into electrical signals;
   g. a liquid medium in liquid contact with both acoustic lenses and wherein the acoustic waves are focused to a microscope waist;
   h. means for moving the object in a plane perpendicular to the direction of the acoustic waves and through the microscopic cross-sectional area of the waist formed by the acoustic lenses so that the object modulates the acoustic waves and the electrical signals from the transducer means converted therefrom; and
   i. means for obtaining a two dimensional, high resolution picture of the object wherein the contrast of the picture at predetermined locations corresponds to changes in the phase difference between the electrical signals after conversion of the acoustic waves as modulated by the object and corresponding electrical signals not modulated by the object, said predetermined locations corresponding to the position of the object as determined by the moving means.

18. The apparatus of claim 17 wherein the picture obtaining means includes means for comparing the phase difference between the electrical signals after conversion of the acoustic waves as modulated by the object and the electrical signals not modulated by the object.

19. The apparatus of claim 17 wherein the moving means translates the object in a raster pattern and the picture means includes a CRT display with a raster synchronized with the translation of the object.

20. The apparatus of claim 17 wherein the first and second acoustic media are disposed to reflect acoustic waves from the object and said picture means display an optical density corresponding to the acoustic energy reflected by the object.

21. A microscope for obtaining a two dimensional, pictorial representation of an object of interest by scanning the object with ultrasonic acoustic waves, comprising:
   a. a first single-surface acoustic lens assembly having a concave spherical surface at one end with a predetermined focal point;
   b. a transmitting transducer attached to the first acoustic lens assembly and generating plane acoustic waves therein, the concave surface of the first acoustic lens focuses the plane acoustic waves to a waist having a microscopic cross-sectional area; said waves having a frequency of at least 100 MHz;
   c. a second single-surface acoustic lens assembly having a concave spherical surface at one end with a predetermined focal point, said first and second lenses being positioned so that their foci are coincident;
   d. a liquid medium in liquid contact with both of the acoustic lenses and wherein the acoustic waves are focused to a microscopic waist;
   e. means for moving the object in a raster pattern perpendicular to the direction of the acoustic waves and through the microscopic cross-sectional area of the waist formed by the acoustic lenses so that the object modulates the acoustic beam;
   f. a detecting transducer attached to the second acoustic lens assembly for receiving the acoustic waves modulated by the object and recollimated by the second acoustic lens, said transducer having output signals corresponding to the modulation of the acoustic waves by the object; and
   g. display means having a raster trace synchronized to the raster pattern of the moving means and connected to the detecting transducer so that the output signals therefrom produce a two dimensional, high resolution visual pattern corresponding to the modulation of the acoustic beam by the object.

22. The apparatus of claim 21 wherein the display means produces a visual pattern having a contrast at predetermined locations corresponding to changes in the intensity of the output signals obtained from the detecting transducer, said predetermined locations corresponding to the position of the object as determined by the moving means.

23. The apparatus of claim 21 wherein the display means produces a visual pattern having a contrast at predetermined locations corresponding to changes in the phase difference between the output signals obtained from the detecting transducer and corresponding signals not modulated by the object, said predetermined locations corresponding to the position of the object as determined by the moving means.

24. The apparatus of claim 27 wherein the display means includes a CRT display and the output signals from the detecting transducer modulate the intensity of the electron beam of said CRT display.

25. A microscope for scanning an object with ultrasonic acoustic waves comprising:
   a. a first acoustic medium wherein ultrasonic waves are propagated;
   b. means forming a plurality of acoustic lenses at the end of the first propagating medium, said acoustic lenses being located in laterally spaced apart relationship;
   c. means for generating ultrasonic acoustic waves in the first propagating medium, said waves being directed toward the acoustic lenses and focused therewith;
   d. a second acoustic medium wherein ultrasonic acoustic waves are recollimated;

e. means forming a plurality of acoustic lenses at the end of the second propagating medium, each of said acoustic lenses in the first propagating medium having a corresponding acoustic lens in the second propagating medium and each pair of corresponding lenses having coincident foci;

f. means for moving the object in sequence through said acoustic beams;

g. means for detecting the perturbed acoustic energy from each of said beams;

h. means for time delaying the detected acoustic signals in a fashion correlated with the detection intervals;

i. means for combining the detected signals from all of said acoustic beams; and j. means for displaying the combined signals from all of said beams.

26. A microscope for scanning an object with ultrasonic acoustic waves, comprising:

a. a first acoustic medium wherein ultrasonic waves are propagated;

b. means forming a plurality of acoustic lenses at the end of the first propagating medium;

c. means for generating ultrasonic acoustic waves in the first propagating medium, said waves being directed toward each of said acoustic lenses and focused thereby into a plurality of focal points located on a common plane;

d. a second acoustic medium wherein ultrasonic acoustic waves are recollimated;

e. means forming a plurality of acoustic lenses at the end of the second acoustic medium, each of said acoustic lenses in the first acoustic medium having a corresponding acoustic lens in the second medium and both corresponding lenses having coincident foci;

f. means for moving the object into interception with at least one acoustic beam;

g. means for detecting the acoustic signals resulting from said first and second acoustic beams;

h. means for comparing the phase of the first and second detected acoustic signals; and i. means for displaying the phase comparisons between said detected acoustic signals.

27. Method for obtaining a two dimensional, pictorial representation of an object of interest by scanning the object with ultrasonic acoustic waves, comprising the steps of:

a. generating acoustic waves having a frequency of at least 100 MHz in an acoustic propagating medium with a transducer;

b. focusing the waves to a waist having a microscopic cross-sectional area with a concave acoustic lens located at one end of the propagating medium;

c. translating the object through a microscopic cross-sectional area of the waist in a raster pattern perpendicular to the direction of the focused acoustic waves;

d. modulating the focused acoustic waves with the translated object;

e. recollimating the acoustic waves modulated by the object;

f. detecting the recollimated acoustic waves with a second transducer; and g. displaying a two dimensional, high resolution picture of said object wherein said picture has an optical density at predetermined locations thereon corresponding to the detected acoustic waves at corresponding locations on said object.

28. The method of claim 27 further including the step of synchronizing the raster pattern of the translation of the object with the display of the picture, said display having a corresponding raster.

29. The acoustic microscope of claim 47 including a second solid acoustic propagating medium wherein said acoustic energy waves are recollimated, means for forming a second acoustic lens at the end of said second propagating medium, said first and second acoustic lenses having coincident foci, and transducer means for converting the acoustic energy waves in the second acoustic medium into electrical signals and said fluid medium is in contact with both acoustic lenses whereby said reflected acoustic energy is isolated from said transmitted energy.

30. An acoustic microscope for producing an image of an object of interest utilizing high frequency acoustic wave energy, comprising:

a. transducer means for generating acoustic energy at a frequency of at least 100 MHz.

b. means forming a solid acoustic energy propagating medium having a predetermined acoustic velocity C1 disposed adjacent said acoustic energy generating means, said transducer means and propagating medium forming a collimated beam of acoustic energy;

c. a first acoustic lens means disposed adjacent the other end of said acoustic energy propagating medium, said acoustic means forming a focal point outside of said acoustic energy propagating means, said lens having a predetermined $f$ number;

d. a fluid acoustic energy propagating medium having a predetermined acoustic velocity C2, disposed adjacent said acoustic lens means and within which the focal point of said acoustic lens means occurs and within which an object to be observed may be positioned, said fluid medium having an acoustic velocity to provide a wavelength of said acoustic energy of about 15 microns or less in said medium and substantially less than the acoustic velocity of said acoustic energy propagating medium, said velocity C1 and C2 being chosen such that their ratio produces an acoustical optical system having negligible spherical aberration;

e. means for moving, relatively, said object to be observed with respect to the beam such that the focal point of said acoustic lens occurs on the surface or within the object to be observed;

f. a second acoustic lens in said propagating medium at a position to receive acoustic energy reflected from the object; and g. transducer means operatively connected to said second acoustic lens for detecting the acoustic energy perturbed by said object so that an image of the object of interest is obtainable.

31. A method as in claim 27 for obtaining a pictorial representation of an object of biological origin wherein the step of focusing includes focusing the acoustic waves on an object of biological origin and the step of translating includes translating an object of biological origin in a raster pattern.

32. The apparatus of claim 7 wherein the first acoustic medium has an acoustic velocity of C1 and the fluid medium has an acoustic velocity of C2 and the two media are selected such that the ratio C1/C2 is sufficiently large to substantially eliminate spherical aberration.

33. The apparatus of claim 21 wherein the first acoustic medium has an acoustic velocity of C1 and the fluid medium has an acoustic velocity of C2 and the two media are selected such that the ratio C1/C2 is sufficiently large to substantially eliminate spherical aberration.

34. An acoustic microscope for producing an image of an object of interest utilizing high frequency acoustic wave energy, comprising:
 a. transducer means for generating acoustic energy at a frequency of at least 100 MHz and for detecting acoustic energy reflected from the object;
 b. means forming a solid acoustic energy propagating medium having a predetermined acoustic velocity C1 disposed adjacent said acoustic energy generating means, said transducer means and propagating medium forming a collimated beam of acoustic energy;
 c. an acoustic lens means disposed adjacent the other end of said acoustic energy propagating medium, said acoustic lens means forming a focal point outside of said acoustic energy propagating means, said lens having a predetermined $f$ number and receives acoustic energy reflected from the object;
 d. a fluid acoustic energy propagating medium having a predetermined acoustic velocity C2, disposed adjacent said acoustic lens means and within which the focal point of said acoustic lens means occurs and within which an object to be observed may be positioned, said fluid medium having an acoustic velocity to provide a wavelength of said acoustic energy of about 15 microns or less in said medium and substantially less than the acoustic velocity of said acoustic energy propagating medium, said velocity C1 and C2 being chosen such that their ratio produces an acoustical optical system having negligible spherical aberration; and
 e. means for moving, relatively, said object to be observed with respect to the beam such that the focal point of said acoustic lens occurs on the surface or within the object to be observed, said transducer means being disposed on said acoustical energy propagating medium, in alignment with said lens and said object so that an image of the object of interest is obtainable.

* * * * *

UNITED STATES PATENT OFFICE
CERTIFICATE OF CORRECTION

Patent No. 4,028,933     Dated June 14, 1977

Inventor(s) Ross A. Lemons et al.

It is certified that error appears in the above-identified patent and that said Letters Patent are hereby corrected as shown below:

Column 5, line 51, after "portion" insert -- or section --.

Column 6, line 62, "30" should read -- 80 --.

Column 12, line 7, "47" should read -- 30 --.

Column 12, line 65, "7" should read -- 17 --.

This certificate supersedes Certificate of Correction issued October 11, 1977.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks